United States Patent
Long et al.

(10) Patent No.: US 9,771,529 B2
(45) Date of Patent: *Sep. 26, 2017

(54) PROCESS FOR PRODUCING LIGHT OLEFINS AND AROMATICS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Jun Long, Beijing (CN); Zhijian Da, Beijing (CN); Dadong Li, Beijing (CN); Xieqing Wang, Beijing (CN); Xingtian Shu, Beijing (CN); Jiushun Zhang, Beijing (CN); Hong Nie, Beijing (CN); Chaogang Xie, Beijing (CN); Zhigang Zhang, Beijing (CN); Wei Wang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 586 days.

This patent is subject to a terminal disclaimer.

(21) Appl. No.: 14/292,945

(22) Filed: Jun. 2, 2014

(65) Prior Publication Data

US 2014/0275673 A1    Sep. 18, 2014

Related U.S. Application Data

(62) Division of application No. 10/592,166, filed as application No. PCT/CN2005/000281 on Mar. 8, 2005, now Pat. No. 8,778,170.

(30) Foreign Application Priority Data

Mar. 8, 2004  (CN) .......................... 2004 1 0006189
Jul. 14, 2004  (CN) .......................... 2004 1 0068934

(51) Int. Cl.
  *C10G 69/04*  (2006.01)
  *C10G 69/06*  (2006.01)
  (Continued)

(52) U.S. Cl.
  CPC ............... *C10G 69/04* (2013.01); *C07C 4/06* (2013.01); *C07C 5/05* (2013.01); *C07C 5/11* (2013.01);
  (Continued)

(58) Field of Classification Search
  CPC ........ C10G 69/02; C10G 69/04; C10G 69/06; C10G 69/14
  See application file for complete search history.

(56) References Cited

U.S. PATENT DOCUMENTS 3,775,290 A  * 11/1973  Peterson ................ C10G 69/04
                                                208/50
3,862,254 A  *  1/1975  Eisenlohr ................ C07C 4/18
                                                585/489

(Continued)

FOREIGN PATENT DOCUMENTS

CN    1215041 A    4/1999
CN    1217366 A    5/1999
(Continued)

OTHER PUBLICATIONS

PCT/CN2005/000281 International Search Report, dated Jun. 16, 2005.
(Continued)

*Primary Examiner* — Renee Robinson
(74) *Attorney, Agent, or Firm* — Novick, Kim & Lee, PLLC; Allen Xue

(57) ABSTRACT

A process for producing light olefins and aromatics, which comprises reacting a feedstock by contacting with a catalytic cracking catalyst in at least two reaction zones, wherein the (Continued)

reaction temperature of at least one reaction zone among the reaction zones downstream of the first reaction zone is higher than that of the first reaction zone and its weight hourly space velocity is lower than that of the first reaction zone, separating the spent catalyst from the reaction product vapor, regenerating the separated spent catalyst and returning the regenerated catalyst to the reactor, and separating the reaction product vapor to obtain the desired products, light olefins and aromatics. This process produces maximum light olefins such as propylene, ethylene, etc from heavy feedstocks, wherein the yield of propylene exceeds 20% by weight, and produces aromatics such as toluene, xylene, etc at the same time.

8 Claims, 4 Drawing Sheets

(51) Int. Cl.
| | |
|---|---|
| *C10G 69/14* | (2006.01) |
| *C10G 69/02* | (2006.01) |
| *C10G 11/18* | (2006.01) |
| *C07C 4/06* | (2006.01) |
| *C07C 5/05* | (2006.01) |
| *C07C 5/11* | (2006.01) |

(52) U.S. Cl.
CPC .............. *C10G 11/18* (2013.01); *C10G 69/02* (2013.01); *C10G 69/06* (2013.01); *C10G 69/14* (2013.01); *C10G 2300/107* (2013.01); *C10G 2300/1044* (2013.01); *C10G 2300/1055* (2013.01); *C10G 2300/1074* (2013.01); *C10G 2300/1077* (2013.01); *C10G 2300/301* (2013.01); *C10G 2300/4006* (2013.01); *C10G 2300/4018* (2013.01); *C10G 2300/4093* (2013.01); *C10G 2300/44* (2013.01); *C10G 2300/807* (2013.01); *C10G 2400/20* (2013.01); *C10G 2400/30* (2013.01)

(56) References Cited

U.S. PATENT DOCUMENTS

| | | | |
|---|---|---|---|
| 3,894,934 A | 7/1975 | Owen et al. | |
| 3,928,172 A | 12/1975 | Davis, Jr. et al. | |
| 4,090,948 A | 5/1978 | Schwarzenbek | |
| 4,218,306 A | 8/1980 | Gross et al. | |
| 4,225,418 A * | 9/1980 | Hilfman | B01J 29/076 |
| | | | 208/111.15 |
| 4,980,053 A | 12/1990 | Li et al. | |
| 5,154,818 A | 10/1992 | Harandi et al. | |
| 5,582,714 A | 12/1996 | Forte | |
| 5,685,972 A | 11/1997 | Timken et al. | |
| 5,773,676 A * | 6/1998 | Drake | C10G 59/02 |
| | | | 208/64 |
| 6,113,776 A | 9/2000 | Upson | |
| 6,123,830 A | 9/2000 | Gupta et al. | |
| 6,149,800 A | 11/2000 | Iaccino et al. | |
| 2005/0150817 A1* | 7/2005 | Tallman | C10G 51/06 |
| | | | 208/78 |

FOREIGN PATENT DOCUMENTS

| | | | |
|---|---|---|---|
| CN | 1490383 A | 4/2004 | |
| DE | 287948 B5 | 9/1996 | |
| EP | 0325437 A2 | 7/1989 | |
| EP | 0381870 A1 | 8/1990 | |
| JP | 10-46160 A | 2/1998 | |
| JP | 2002-504169 A | 2/2002 | |
| KR | 10-0253887 B1 | 4/2000 | |
| WO | 98/56873 A1 | 12/1998 | |
| WO | WO 98/56873 * | 12/1998 | ............. C10G 11/00 |
| WO | 00/31215 A1 | 6/2000 | |

OTHER PUBLICATIONS

PCT/CN2005/000281 International Preliminary Report on Patentability, dated Sep. 13, 2006.
EP 05714812 Supplementary European Search Report, dated Feb. 27, 2012.

* cited by examiner

PROCESS FOR PRODUCING LIGHT OLEFINS AND AROMATICS

TECHNICAL FIELD

The present invention pertains to a process for the catalytic conversion of hydrocarbon oils in the absence of hydrogen and, more particularly, it pertains to a process for converting heavy feedstocks into light olefins rich in propylene and ethylene and aromatics rich in toluene and xylene.

BACKGROUND

Light olefins such as ethylene, propylene, etc are important chemical feedstocks, wherein propylene is a synthetic monomer of the products such as polypropylene, acrylonitrile, etc. Along with the rapid increase of the demand for the derivatives such as polypropylene, etc, the demand for propylene is also rapidly increasing year by year. The demand of the world market for propylene already increased from 15.2 million tons of 20 years ago to 51.2 million tons of 2000 with an average annual increase rate of 6.3%. It is predicted that the demand for propylene will have attained 86 million tons by 2010 with an average annual increase rate of 5.6%.

The process for producing propylene is mainly steam cracking and catalytic cracking (FCC), wherein steam cracking uses light oils such as naphtha, etc. as feedstocks to produce ethylene and propylene by thermal cracking with a propylene yield of only about 15% by weight, while FCC uses heavy oils such as vacuum gas oil (VGO) as a feedstock. Presently, 66% propylene in the world comes from the byproducts of steam cracking for producing ethylene, 32% comes from the byproducts of FCC of refineries for producing naphtha and diesel, and a small amount (about 2%) is obtained from the dehydrogenation of propane and metathesis of between ethylene and butene.

If the petrochemical industry produces ethylene and propylene through the conventional steam cracking route, several restrictive factors would be faced such as shortage of light feedstocks, deficiency of the processing capacity, and high production cost.

FCC is drawing increasing attention due to its advantages of wide adaptability, flexible operation, etc. In the United States of America, almost 50% of the demand of the market for propylene comes from FCC units. The development of the improved techniques of catalytic cracking for increasing the production of propylene is very rapid.

U.S. Pat. No. 4,980,053 discloses a conversion process for producing light olefins from hydrocarbons, wherein the feedstocks are petroleum fractions, residuum, or crude oil with different boiling ranges and the converting reaction is carried out in a fluidized bed or moving bed reactor under the conditions of a temperature between 500° C. to 650° C., a pressure between $1.5 \times 10^5$ and $3 \times 10^5$ Pa, a WHSV between 0.2 $h^{-1}$ and 2.0 $h^{-1}$, and a catalyst to oil ratio between 2 and 12 by using a solid acid catalyst. The catalyst returns to the reactor for cycle use after being regenerated by burning off coke. By this process, the total yield of propylene and ethylene may attain about 40%, wherein the yield of propylene is up to 26.34%.

WO 00/31215A1 discloses a catalytic cracking process for producing olefins, which uses a catalyst with ZSM-5 and/or ZSM-11 zeolites as active components and a great amount of inert substances as substrates, and uses VGO as a feedstock. The yield of propylene does not exceed 20% by weight.

U.S. Pat. No. 6,123,830 discloses a combination process consisting of two-stage catalytic cracking and two-stage hydrotreating, the objective of which is to produce as much olefins as possible and improve the quality of oil distillates and octane number of naphtha. The feedstock is converted into the first hydrotreated product in the first hydrotreating unit, and the first hydrotreated product enters the first catalytic cracking unit, wherein naphtha, diesel, and heavy oil are obtained by using a catalyst with an intermediate pore size zeolite as a main active component. The heavy oil enters the second hydrotreating unit for hydrogenation to obtain the second hydrotreated product, and the second hydrotreated product enters the second catalytic cracking unit for cracking, wherein the active component of the catalyst is mainly an intermediate pore size zeolite. The yield of propylene in this process is rather low.

Aromatics are also important chemical feedstocks, in particular, light aromatics such as BTX (benzene, toluene, and xylene), which are used to produce synthetic materials such as chemical fibers, plastics, etc. Presently, the major process for producing aromatics is catalytic reforming, wherein the feedstock should be fed to strict pretreatment because the active components of the reforming catalyst are noble metals. Disadvantageously the process flow of the movement and regeneration of the reforming catalyst is complicated.

The above references produce propylene only as a byproduct with low yields not exceeding 30% and at the same time that naphtha and diesel are produced. Several of the references only can produce aromatics, but cannot produce light olefins and aromatics simultaneously. In order to meet the increasing demand for the chemical feedstocks, propylene, ethylene, aromatics, etc, there is a necessity to develop a chemical industry type oil refining process for simultaneously producing large amounts of propylene, ethylene, and aromatics from heavy feedstocks.

SUMMARY

The current disclosure provides several processes for simultaneously producing propylene, ethylene, and aromatics from heavy feedstocks, the yield of propylene in these processes being higher than 20%.

Technical Scheme 1

In one aspect, the process for producing light olefins and aromatics includes a feedstock that comes into contact with a catalytic cracking catalyst and reacts under the conditions of a reaction temperature between 400° C. and 800° C., and a WHSV between 0.1 $h^{-1}$ and 750 $h^{-1}$. The reaction is carried out in at least two reaction zones, and the reaction temperature of at least one reaction zone among the reaction zones at the down stream side of the first reaction zone is higher than that of the first reaction zone and its WHSV is lower than that of the first reaction zone. Spent catalyst is separated from the reaction product vapor and the catalyst returns to the reactor after being regenerated. The reaction product vapor is separated to obtain the desired products, light olefins and aromatics.

Technical Scheme 2

In another aspect, the process for producing light olefins and aromatics includes a first step of feeding a feedstock and an optional cycle material into a hydrotreating unit for contact with a hydrotreating catalyst and hydrogen, and reaction under the conditions of a hydrogen partial pressure between 3.0 MPa and 20.0 MPa, a reaction temperature between 300° C. and 450° C., a hydrogen/oil ratio between 300 and 2000 by volume, and a LHSV between 0.1 $h^{-1}$ and 3.0 $h^{-1}$, The reaction effluent is then separated to obtain hydrotreated product, with hydrogen being cycled for reuse;

In a second step, the hydrotreated product is reacted with a catalytic cracking catalyst under the conditions of a reaction temperature between 400° C. and 800° C., and a WHSV between 0.1 $h^{-1}$ and 750 $h^{-1}$. The reaction is carried out in at least two reaction zones, and the reaction temperature of at least one reaction zone among the reaction zones at the down stream side of the first reaction zone is higher than that of the first reaction zone and its WHSV is lower than that of the first reaction zone. The spent catalyst is separated from the reaction product vapor and the catalyst returns to the reactor after being regenerated. The reaction product vapor is separated to obtain desired products, light olefins and aromatics.

Technical Scheme 3

In another aspect, the process for producing light olefins and aromatics includes a first step of contacting a feedstock with hydrogen for reaction with a hydrotreating catalyst under the conditions of a hydrogen partial pressure between 3.0 MPa and 20.0 MPa, a reaction temperature between 300° C. and 450° C., a hydrogen/oil ratio between 300 and 2000 by volume, and a LHSV between 0.1 $h^{-1}$-3.0 $h^{-1}$ The reaction effluent is then separated to obtain $H_2$, $CH_4$, hydrotreated $C_2^0$-$C_4^0$, hydrotreated naphtha, and hydrotreated product, with hydrogen being cycled for reuse;

In a second step, the hydrotreated product of the first step is reacted with a catalytic cracking catalyst under the conditions of a reaction temperature between 400° C. and 800° C. and a WHSV between 0.1 $h^{-1}$-750 $h^{-1}$. The reaction is carried out in at least two reaction zones, and the reaction temperature of at least one reaction zone among the reaction zones at the down stream side of the first reaction zone is higher than that of the first reaction zone and its WHSV is lower than that of the first reaction zone. The spent catalyst is separated from the reaction product vapor and returns to all or a part of the reaction zones of step (2) after being stripped and regenerated. The reaction product vapor is separated to obtain $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, LCO, and heavy cycle oil, wherein $C_2^=$-$C_3^=$ are a part of the desired products and catalytic cracking $C_4$-$C_5$ are cycled back to the catalytic cracking reactor;

In a third step, the hydrotreated $C_2^0$-$C_4^0$ and hydrotreated naphtha of the first step and catalytic cracking $C_2^0$-$C_3^0$ of the second step are treated with steam under a temperature between 700° C.–1000° C., and the reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, and fuel oil, wherein the steam cracking $C_2^=$-$C_3^=$ are a part of the desired products and the steam cracking $C_4$-$C_5$ are cycled back to the catalytic cracking reactor;

In a fourth step, the catalytic cracking naphtha of the second step and steam cracking naphtha of the third step are selectively hydrogenated, and then fed to solvent extraction to obtain aromatics and extraction raffinate, wherein the aromatics are a part of the desired products, and the extraction raffinate returns to the third step as one of the feedstocks of the steam cracking.

In one example an apparatus for producing light olefins and aromatics includes a hydrotreating unit, wherein $H_2$, $CH_4$, hydrotreated $C_{20}$-$C_{40}$, hydrotreated naphtha, and hydrotreated product are obtained after a feedstock comes into contact with hydrogen and a hydrotreating catalyst.

A catalytic cracking unit for reacting the hydrotreated product with a catalytic cracking catalyst. The reaction is carried out in at least two reaction zones, and the reaction temperature of at least one reaction zone among the reaction zones downstream of the first reaction zone is higher than that of the first reaction zone and its WHSV is lower than that of the first reaction zone. The spent catalyst is separated from the reaction product vapor, wherein the catalyst returns to all or a part of the reaction zones of the second step form above after being stripped and regenerated, and the reaction product vapor is separated to obtain $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, LCO, and HCO. The $C_2^=$-$C_3^=$ are a part of the desired products, and the catalytic cracking $C_4$-$C_5$ are cycled back to the catalytic cracking reactor;

A steam cracking unit for reacting the hydrotreated $C_2^0$-$C_4^0$, hydrotreated naphtha, and catalytic cracking $C_2^0$-$C_3^0$ with steam under a temperature between 700° C. and 1000° C. and the reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, and fuel oil, wherein the steam cracking $C_2^=$-$C_3^=$ are a part of the desired products;

A selective hydrogenation unit for selectively hydrogenating wherein the catalytic cracking naphtha and the steam cracking naphtha to obtain the selectively hydrotreated naphtha;

A solvent extraction unit for selectively extracting hydrotreated naphtha to obtain aromatics and extraction raffinate. The aromatics are a part of the desired products, and the extraction raffinate returns to the steam cracking unit as one of the feedstocks for steam cracking.

BRIEF DESCRIPTION OF THE DRAWINGS

The teachings of the present invention can be readily understood by considering the following detailed description in conjunction with the accompanying drawings.

DETAILED DESCRIPTION

Figure 1:
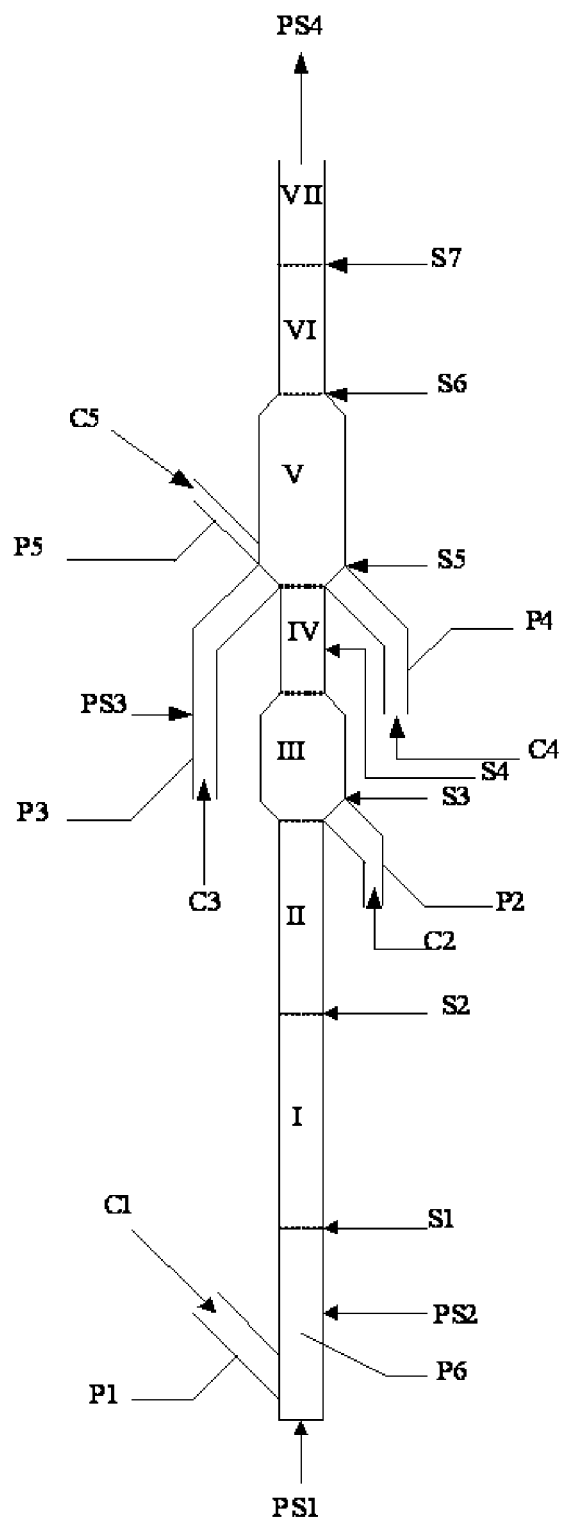
FIG. 1 is a schematic diagram of an example catalytic cracking process of technical scheme 1.

In one example, a process for producing light olefins and aromatics includes a feedstock that comes into contact with a catalytic cracking catalyst and reacts under a reaction temperature between 400° C. and 800° C., and a WHSV between 0.1 $h^{-1}$ and 750 $h^{-1}$. The reaction is carried out in at least two reaction zones, and the reaction temperature of at least one reaction zone among the reaction zones downstream of the first reaction zone is higher than that of the first reaction zone and its WHSV is lower than that of the first reaction zone. Spent catalyst is separated from the reaction product vapor and the catalyst returns to the reactor after being regenerated. The reaction product vapor is separated to obtain the desired products, light olefins and aromatics.

1) Feedstock

In one particular example, the feedstocks in each reaction zone are petroleum hydrocarbons, other mineral oils, or both, wherein the petroleum hydrocarbon is one selected from the group consisting of vacuum gas oil (VGO), atmospheric gas oil (AGO), coked gas oil (CGO), deasphalted oil (DAO), vacuum residuum (VR), atmospheric residuum (AR), cycle oil, slurry, diesel, naphtha, hydrocarbons with 4-8 carbon atoms, alkanes with 2-3 carbon atoms or mixtures thereof and the other mineral oil is liquid products from coal liquefaction, tar sand oil, or shale oil.

In one example, the feedstock of the first reaction zone is one selected from the group consisting of vacuum gas oil, atmospheric gas oil, coked gas oil, deasphalted oil, vacuum residuum, atmospheric residuum, cycle oil, slurry, diesel, naphtha or mixture thereof.

The feed of reaction zones downstream of the first reaction zone is one selected from the group consisting of cycle oil, slurry, diesel, naphtha, hydrocarbons with 4-8 carbon atoms, alkanes with 2-3 carbon atoms or mixture thereof.

The VGO, AGO, CGO, DAO, VR, AR, diesel, and naphtha are unhydrotreated or hydrotreated whole fraction or partial fraction.

The naphtha is one selected from catalytic cracking naphtha, catalytic cracking naphtha, straight-run naphtha, coked naphtha, steam cracking naphtha, thermal cracking naphtha, and hydrotreated naphtha, or mixtures thereof, wherein catalytic cracking naphtha may be either from the catalytic cracking process of the present invention, or from conventional catalytic cracking, straight-run naphtha, coked naphtha, steam cracking naphtha, thermal cracking naphtha, and hydrotreated naphtha are from outside of the present process.

The diesel is one selected from catalytic cracking LCO, straight-run diesel, coked diesel, thermal cracking diesel, and hydrotreated diesel obtained by the present process, or mixtures thereof, wherein catalytic cracking LCO may be either from the catalytic cracking process of the present invention, or from conventional catalytic cracking, straight-run diesel, coked diesel, thermal cracking diesel, and hydrotreated diesel are from outside of the present process.

The hydrocarbons with 4-8 carbon atoms and alkanes with 2-3 carbon atoms can be either from the catalytic cracking process of the present invention, or from conventional catalytic cracking, coking, thermal cracking, hydrogenating, etc. processes.

The feedstock of each reaction zone may be identical, or different. In one example, the feedstock of the first reaction zone is a heavier hydrocarbon, such as VGO, AGO, CGO, DAO, VR, AR, self-produced cycle oil, self-produced slurry, outside cycle oil, outside slurry, diesel, and naphtha. The reaction zone with higher reaction temperature is a lighter hydrocarbon, such as hydrocarbons with 4-8 carbon atoms, alkanes with 2-3 carbon atoms, naphtha, and diesel.

2) Catalytic Cracking Catalyst

In this example, the catalytic cracking catalyst comprises zeolite, inorganic oxide, and optionally, clay, which accounts for the following percent of the total weight of the catalyst respectively: about 10%-50% zeolite by weight, about 5%-90% inorganic oxide by weight, and about 0%-70% clay by weight. The term "about" as used in this description is relative to percentages or compositions refers to possible variations in the compositional percentages, such as normally accepted variations or tolerances in the art.

The zeolite is an active component, which is selected from intermediate pore size zeolite, and optionally, large pore zeolite. In one example, the intermediate pore size zeolite accounts for about 25%-100%, preferably about 50%-100% of the total weight of the zeolite and the large pore zeolite accounts for about 0%-75%, preferably 0%-50% of the total weight of the zeolite. The intermediate pore size zeolite is selected from ZSM series zeolites and/or ZRP zeolites, or ZSM and ZRP zeolites modified with nonmetal elements such as phosphor and/or transition metal elements such as iron, cobalt, and nickel U.S. Pat. No. 5,232,675 discloses further description of ZRP zeolites. The ZSM series zeolite is one selected from the group consisting of ZSM-5, ZSM-11, ZSM-12, ZSM-23, ZSM-35, ZSM-38, and ZSM-48, and other zeolites with similar structure, or mixtures thereof. U.S. Pat. No. 3,702,886 discloses further description of ZSM-5 zeolites. In this example, the large pore zeolite is one selected from the group consisting of rare-earth Y (REY), rare-earth HY(REHY), ultrastable Y and high silica Y obtained by different processes or mixtures thereof.

The inorganic oxide as a binder is selected from silica ($SiO_2$) and/or alumina ($Al_2O_3$).

Clay as a matrix (i.e. supporter) is selected from kaolin and/or halloysite.

The catalytic cracking catalyst in each reactor may be identical or different.

3) Catalytic Cracking Reactor

The cracking reactor comprises at least two, preferably 2-7, and more preferably 2-3 reaction zones. Each reaction zone is one selected from riser, fluidized bed, ascending transfer line, descending transfer line, and moving bed or some part thereof. The connections between the various reaction zones are series, parallel, or series-parallel. The riser can be the conventional unidiameter, or various types of tapered risers. The structure and dimension of each reaction zone may be identical or different, wherein the velocity of the gas in the fluidized bed is between about 0.1 m/s-2.4 m/s (catalyst is neglected).

In this example, the first reaction zone is a zone wherein a feedstock with a boiling range between about 25° C.-1200° C. comes into contact with the catalyst. The feedstock for the first reaction zone may also be a feedstock of the conventional catalytic cracking wherein a small amount of light hydrocarbons with boiling points lower than those of the feedstock of the conventional catalytic cracking such as $C_2$-$C_6$ may be incorporated. There may be other reaction zones upstream side of this reaction zone. The feedstock of the conventional catalytic cracking is one selected from the group consisting of vacuum gas oil, atmospheric gas oil, coked gas oil, deasphalted oil, vacuum residuum, atmospheric residuum, cycle oil, slurry, diesel, naphtha or mixture thereof.

The first reaction zone is preferably riser, ascending transfer line, descending transfer line, or fluidized bed, and more preferably riser or fluidized bed. The other reaction zone is preferably fluidized bed, riser, or moving bed, and more preferably fluidized bed or riser.

4) Operating Conditions

In one example, the operating conditions include a reaction temperature of about 400° C.-800° C., preferably about 500° C.-700° C., a WHSV of about 0.1 $h^{-1}$-750 $h^{-1}$, preferably about 1 $h^{-1}$-500 $h^{-1}$, a reaction pressure of about 0.10 MPa-1.0 MPa (absolute pressure), ratio of catalytic cracking catalyst to feedstock about 1-150 by weight. According to the common knowledge of the ordinary in the art, the reaction temperature of a tube reactor such as riser reactor means the outlet temperature, and the reaction temperature of a bed reactor such as fluidized bed reactor means the average temperature of the bed.

In order to realize the fluidized operation, a lifting medium may be injected from the bottom of the reaction zone and the lifting medium is selected from steam or dry gas with steam being preferred. The ratio of steam to the feedstock is about 0.05-1.0 by weight.

The reaction temperature of at least one, preferably 1-6, and more preferably 1-2 reaction zones out of the reaction zones downstream of the first reaction zone is higher than that of the first reaction zone. The difference between the reaction temperature of the reaction zone with a higher reaction temperature and that of the first reaction zone is about 10° C.-200° C., preferably about 20° C.-100° C.

In order that the reaction temperature of at least one reaction zone out of the reaction zones downstream of the first reaction zone is higher than that of the first reaction zone, heat is supplemented to the above reaction zone by means of one or more of the ways selected form supplying hot regenerated catalyst, hot coke deposited catalyst, hot fresh catalyst, and hot feedstock to the reaction zone, or equipping heating coil pipes in the reaction zone. The total heat supplemented accounts for about 10%-80%, and preferably about 20%-60% of the reaction heat of the total reaction system.

The WHSV of at least one, preferably 1-6, and more preferably 1-2 reaction zones out of the reaction zones downstream of the first reaction zone is lower than that of the first reaction zone, and ratio of the WHSV of this reaction zone to that of the first reaction zone is about 1:1.1-1:750, and preferably about 1:1.1-1:300.

The spent catalyst is separated from reaction product vapor by conventional disengaging, cyclone separation and the catalyst returns to the reactor after being regenerated by burning off coke, before which the catalyst is optionally fed to stripping.

5) Separation of the Product

The product includes light olefins, such as ethylene, propylene, and optionally, butene.

The process for separating ethylene from the reaction product vapor is the same as that for separating ethylene, which is well known to the ordinary skilled in the art, and the process for separating propylene and optionally, butene from the reaction product vapor is the same as that for separating propylene and butane, which is well known to the ordinary skilled in the art. The process for separating aromatics from the cracking naphtha fraction of the reaction product vapor is the same as that for separating aromatics, which is well known to the ordinary skilled in the art, i.e. extraction. Before separating aromatics from the catalytic cracking naphtha obtained by the present process, $C_5$-$C_8$ in this naphtha may be separated first as a recycle stream.

An example technical scheme for separating the product includes the following steps.

(1) The feedstock and steam enters the first reaction zone, i.e. the riser, come into contact with a regenerated and/or fresh catalytic cracking catalyst, or both, and reacts under the conditions of a reaction temperature between about 500° C. and about 700° C., a WHSV between about 0.1 $h^{-1}$ and about 750 $h^{-1}$, a reaction pressure between about 0.1 Mpa and about 1.0 Mpa (absolute pressure), a ratio of the catalytic cracking catalyst to the feedstock between about 1 and about 150 by weight, and a ratio of steam to the feedstock between about 0.05 and about 1.0 by weight;

(2) The reaction effluent from the first reaction zone enters the second reaction zone, i.e. the fluidized bed, comes into contact with the regenerated catalytic cracking catalyst, steam, ethane, propane, $C_4$-$C_8$, and reacts under conditions of a reaction temperature between about 500° C. and about 700° C., a WHSV between about 0.1 $h^{-1}$ and about 750 $h^{-1}$, a reaction pressure between about 0.1 Mpa and about 1.0 Mpa (absolute pressure), a ratio of the catalytic cracking catalyst to feedstock between about 1 and about 150 by weight, and a ratio of steam to feedstock between about 0.05 and about 1.0 by weight. The difference between the reaction temperature of the second reaction zone and that of the first reaction zone is about 10° C.-200° C., preferably about 20° C.-100° C. The ratio of the WHSV of the second reaction zone to that of the first reaction zone is about 1:1.1-1:750, preferably about 1:1.1-1:300;

(3) The spent catalyst in the second reaction zone is separated from the reaction product vapor. The spent catalyst enters the regenerator after stripping and returns to the first reaction zone and the second reaction zone after being regenerated by burning off coke, and the reaction product vapor is separated to obtain the desired products, light olefins and aromatics.

The preferred technical scheme further includes a Step (4), in which the reaction product vapor expect for the desired products, $H_2$ and $CH_4$ are employed as recycle streams, which comprise ethane, propane, $C_4$-$C_6$, the extraction raffinate obtained after the solvent extraction of the naphtha, diesel, cycle oil, and slurry. Ethane, propane, C4-C6, and the extraction raffinate returns to the second reaction zone, and the diesel, cycle oil, and slurry return to the first reaction zone.

Embodiment 2

Another example process for producing light olefins and aromatics includes the following steps.

(1) A feedstock and optionally recycle stream enter the hydrotreating unit and react with a hydrotreating catalyst and hydrogen under the conditions of a hydrogen partial pressure between about 3.0 MPa and about 20.0 MPa, a reaction temperature between about 300° C. and about 450° C., a hydrogen/oil ratio between about 300 and about 2000 by volume, and a LHSV between about 0.1 $h^{-1}$ and about 3.0 $h^{-1}$. The reaction effluent is separated to obtain hydrotreated product and hydrogen is recycled for use.

(2) The hydrotreated product comes into contact with a catalytic cracking catalyst and reacts under the conditions of a reaction temperature between about 400° C. and about 800° C. and a WHSV between about 0.1 $h^{-1}$-750 $h^{-1}$ in at least two reaction zones, wherein the reaction temperature of at least one reaction zone out of the reaction zones downstream of the first reaction zone is higher than that of the first reaction zone, and the WHSV of at least one reaction zone out of the reaction zones downstream of the first reaction zone is lower than that of the first reaction zone. The spent catalyst is separated from the reaction product vapor. The spent catalyst is recycled for use after being regenerated and the reaction product vapor is separated to obtain the desired products, light olefins and aromatics.

This example optionally further includes a step (3) of recycling remaining gases and liquids in the reaction gas-oil except the desired products, $H_2$. and $CH_4$ as recycle streams, wherein the gas recycle streams are ethane, propane, and $C_4$, and the liquid recycle streams are $C_5$-$C_6$, extraction raffinate of the naphtha, recycled oil and slurry. Ethane, propane, and $C_4$-$C_6$, and/or extraction raffinate of naphtha, diesel, cycle oil, and slurry. Ethane, propane, $C_4$-$C_6$, aforesaid extraction raffinate, diesel, or hydrotreated diesel, and slurry return to the reaction zone of step (2), and the cycle oil returns to the hydrotreating unit. The lower alkanes which do not participate reaction are withdrawn from the unit.

In one example, the feedstock is petroleum hydrocarbons other mineral oils, or both, wherein the petroleum hydrocarbon is one selected from the group consisting of VGO, AGO, CGO, DAO, VR, AR, diesel, and naphtha or mixtures thereof, and the other mineral oil is liquid products from coal liquefaction, tar sand oil, or shale oil.

The VGO, AGO, CGO, DAO, VR, AR, diesel, and naphtha are unhydrotreated or hydrotreated whole fraction or partial fraction.

The naphtha is one selected from catalytic cracking naphtha, straight-run naphtha, coked naphtha, steam cracking naphtha, thermal cracking naphtha, and hydrotreated naphtha, or mixtures thereof, wherein catalytic cracking naphtha may be either from the catalytic cracking process of the present invention, or from conventional catalytic cracking, straight-run naphtha, coked naphtha, steam cracking naphtha, thermal cracking naphtha, and hydrotreated naphtha are from outside of the present process.

The diesel is one selected from catalytic cracking LCO, catalytic cracking diesel, straight-run diesel, coked diesel, thermal cracking diesel, and hydrotreated diesel, or mixtures thereof, wherein catalytic cracking LCO may be either from the catalytic cracking process of the present invention, or from conventional catalytic cracking, straight-run diesel, coked diesel, thermal cracking diesel, and hydrotreated diesel are from outside of the present process.

The feedstock and cycle oil in step (1) may enter the hydrotreating reactor together after mixing to reduce the investment on the equipment. The feedstock and cycle oil come into contact with a hydrotreating catalyst and hydrogen, and reacts under the conditions of a hydrogen partial pressure between about 3.0 MPa and about 20.0 MPa, a reaction temperature between about 300° C. and about 450° C., a hydrogen/oil ratio between about 300 and about 2000 by volume, and a LHSV between about 0.1 $h^{-1}$ and about 3.0 $h^{-1}$. The reaction effluent is sequentially fed to high pressure separation, low pressure separation, and product fractionation to obtain hydrotreated product.

In a further example, the heavy oil and cycle oil are hydrotreated to obtain the optimum reaction effect, but the high pressure separation, low pressure separation, and product fractionation systems may be shared. The two reaction systems may use a same pressure level in order to share the compressors of fresh hydrogen and recycle hydrogen. The conditions in the hydrogenation of the feedstock includes a hydrogen partial pressure of about 3.0 MPa-20.0 MPa, a reaction temperature of about 300° C.-450° C., a hydrogen/oil ratio of about 300-2000 by volume, and LHSV of about 0.1 $h^{-1}$-3.0 $h^{-1}$. The conditions of the hydrotreating of the cycle oil include a hydrogen partial pressure of about 3.0 MPa-20.0 MPa, a reaction temperature of about 300° C.-450° C., a hydrogen/oil ratio of about 300-2000 by volume, and a LHSV of about 0.2 $h^{-1}$-2.0 $h^{-1}$.

In one example, the hydrotreating catalyst used in the hydrotreating unit is a catalyst of the non-noble metals of Group VIB, Group VIII, or combination thereof supported on alumina, amorphous silica-alumina, or combination thereof. The non-noble metal of Group VIB is selected from Mo and W, and that of Group VIII is selected from Co and Ni. High hydrosaturation and denitrogenation activities but a low cracking activity are required for this catalyst to reserve long straight chain paraffins in the feedstock as much as possible and produce more propylene in catalytic cracking process. In one example, the catalyst comprises about 0-10% by weight of an additive, about 1-9% by weight of one or more of Group VIII metals, about 12-39% by weight of one or more of Group VIB metals, and the remainder % alumina, amorphous silica-alumina, or a combination thereof as support. The additive is selected from non-metal elements and metal elements such as fluorine, phosphor, titanium, etc.

Compared with the feedstock, the hydrotreated product contains less sulfur, nitrogen, and aromatics, and a higher content of hydrogen, favorable for enhancing the yield of propylene when used as a feedstock for the catalytic cracking unit.

The catalytic cracking catalyst, catalytic cracking reactor, and catalytic cracking operating conditions of the present technical scheme are the same as those of previous examples.

Embodiment 3

Another example process for producing light olefins and aromatics includes the following steps.

(1) A feedstock reacts with hydrogen and a hydrotreating catalyst and reacts under the conditions of a hydrogen partial pressure between about 3.0 MPa and about 20.0 MPa, a reaction temperature between about 300° C. and about 450° C., a hydrogen/oil ratio between about 300-2000 by volume, and a LHSV between about 0.1 $h^{-1}$-3.0 $h^{-1}$. The reaction effluent is then separated to obtain $H_2$, $CH_4$, hydrotreated $C_2^0$-$C_4^0$, hydrotreated naphtha, and hydrotreated product, the hydrotreated product, hydrogen being recycled for use.

(2) The hydrotreated product of step (1) reacts with a catalytic cracking catalyst and reacts under the conditions of a reaction temperature between about 400° C. and 800° C. and a WHSV between about 0.1 $h^{-1}$-750 $h^{-1}$ in at least two reaction zones. The reaction temperature of at least one reaction zone downstream of the first reaction zone is higher than that of the first reaction zone, and the WHSV of at least one reaction zone downstream of the first reaction zone is lower than that of the first reaction zone. Spent catalyst is separated from the reaction product vapor, the spent catalyst returning to all or a part of the reaction zones of step (2) after being stripped and regenerated, and the reaction product vapor being separated to obtain $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, light cycle oil, heavy cycle oil, wherein the $C_2^=$-$C_3^=$ are a part of the desired products and the catalytic cracking $C_4$-$C_5$ are recycled to the catalytic pyrolyzed reactor;

(3) The hydrotreated $C_2^0$-$C_4^0$ of step (1) and catalytic cracking $C_2^0$-$C_3^0$ of step (2) come into contact with steam under a temperature between about 700° C.-1000° C. and the reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, fuel oil, wherein the steam cracking $C_2^=$-$C_3^=$ are a part of the desired products and the steam cracking $C_4$-$C_5$ are recycled to the catalytic cracking reactor;

(4) The catalytic cracking naphtha of step (2) and steam cracking naphtha of step (3) are selectively hydrogenated, and then fed for solvent extraction to obtain aromatics and extraction raffinate, wherein the aromatics are a part of the desired products, the extraction raffinate returning to step (3) as one of the feedstocks of steam cracking.

The feedstock, catalytic cracking catalyst, catalytic cracking reactor, and catalytic cracking operating conditions of this example are the same as those of previous examples.

The solvent used in solvent extraction is one selected from the group consisting of sulfolane, N-methyl pyrrolidone, diethyl glycol ether, triethyl glycol ether, tetraethyl glycol, dimethyl sulfoxide, and N-formyl morpholine and mixtures thereof. The temperature in solvent extraction is about 80-120° C., and the ratio of the solvent to the extracted feedstock is about 2-6 by volume. The extracted oil by solvent extraction is one of the desired products, aromatics and the extraction raffinate, i.e. non-aromatics, is one of the feedstocks for steam cracking.

The feedstocks for steam cracking are the hydrotreated $C_2^0$-$C_4^0$ and hydrotreated naphtha of step (1) and catalytic cracking $C_2^0$-$C_3^0$ of step (2).

The reaction conditions in steam cracking include a temperature of about 700° C.-1000° C., residence time of about 0.05 s-0.6 s, and steam/oil ratio of about 0.1-1.0 by weight.

The reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, fuel oil, wherein the steam cracking $C_2^=$-$C_3^=$ are a part of the desired products. The steam cracking $C_2^0$-$C_3^0$ are recycled to the steam cracking reactor and the steam cracked $C_4$-$C_5$ are recycled to the catalytic pyrolyzed reactor.

The above example process produces light olefins such as propylene, ethylene, etc, from heavy feedstocks by integrating process steps of hydrotreating, catalytic cracking, steam cracking, solvent extraction, etc. The yield of propylene exceeds 30%, and additionally results in production of aromatics such as toluene, xylene, etc.

An example apparatus for producing light olefins includes
(1) hydrotreating unit, wherein $H_2$, $CH_4$, hydrotreated $C_2^0$-$C_4^0$, hydrotreated naphtha, and hydrotreated product are obtained after the feedstock comes into contact with hydrogen and a hydrotreating catalyst.
(2) A catalytic cracking unit reacts the hydrotreated product with a catalytic cracking catalyst under the conditions of a reaction temperature between about 400° C. and about 800° C. and a WHSV between about 0.1 $h^{-1}$-750 $h^{-1}$ in at least two reaction zones, wherein the temperature of at least one reaction zone downstream of the first reaction zone is higher than that of the first reaction zone, and the WHSV of at least one reaction zone downstream of the first reaction zone is lower than that of the first reaction zone. The spent catalyst is separated from the reaction product vapor, the spent catalyst returning to all or a part of the reaction zones of step (2) after being regenerated by stripping and the reaction product vapor being separated to obtain $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, light cycle oil, heavy cycle oil, wherein the $C_2^=$-$C_3^=$ are a part of the desired products and the $C_4$-$C_5$ are recycled to the catalytic cracking reactor;
(3) A stream cracking unit for reacting the hydrotreated $C_2^0$-$C_4^0$, hydrotreated naphtha, catalytic cracking $C_2^0$-$C_3^0$, and catalytic cracking $C_2^0$-$C_3^0$ with steam under a temperature between about 700° C. and about 1000° C. The reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, fuel oil, wherein the steam cracking $C_2^=$-$C_3^=$ are a part of the desired products.
(4) A selective hydrogenation unit selectively hydrogenates the catalytic cracking naphtha and steam cracking naphtha to obtain the selectively hydrotreated naphtha.
(5) solvent extraction unit for extracting the selectively hydrotreated naphtha to obtain aromatics and extraction raffinate, wherein the aromatics are a part of the desired products and the extraction raffinate returns to step (3) as one of the feedstocks of steam cracking.

FIG. 1 illustrates a schematic diagram of the catalytic cracking process of technical scheme 1.

There are 7 reaction zones, wherein the temperatures of both reaction zone III and reaction zone V are higher than that of reaction zone I, and the WHSVs of the reaction zones III and V are lower than that of reaction zone I. Medium PS2, such as propane, is injected from the pre-lifting section of the catalyst P6 at the bottom of reaction zone I to carry out reaction. This pre-lifting section P6 can also be regarded as a reaction zone.

In this example, the process flow is as follows:

Regenerated catalyst C1 from the regenerator enters pre-lifting section of the catalyst P6 at the bottom of reaction zone I through catalyst pipeline P1, reacts with medium PS2 after being lifted by medium PS1. In reaction zone I, feedstock S1 comes into contact with the catalyst and stream from pre-lifting section P6 and reacts under a reaction temperature between about 500° C. and about 650° C., a WHSV between about 2 $h^{-1}$ and about 300 $h^{-1}$, an catalyst/oil ratio between about 3 and about 20 by weight, and a reaction pressure between about 0.12 MPa and about 0.6 MPa (absolute pressure). The reaction product and catalyst then enter reaction zone II together.

In reaction zone II, the $C_4$ hydrocarbons feedstock S2 from other catalytic cracking unit comes into contact with the catalyst and stream from reaction zone 1 and reacts under a reaction temperature between about 490° C. and about 640° C., a WHSV between about 20 $h^{-1}$ and about 750 $h^{-1}$, an catalyst/oil ratio between about 3 and about 20 by weight, and a reaction pressure between about 0.12 MPa and about 0.6 MPa (absolute pressure). The reaction product and catalyst then enter reaction zone III together.

In reaction zone III, the $C_4$ hydrocarbons feedstock S3 from the present process comes into contact with the catalyst and stream from reaction zone II and the regenerated catalyst from pipeline P2 and reacts under a reaction temperature between 510° C. and 660° C., a WHSV between about 2 $h^{-1}$ and about 150 $h^{-1}$, an catalyst/oil ratio between about 3 and about 20 by weight, and a reaction pressure between about 0.12 MPa and about 0.6 MPa (absolute pressure). The reaction product and catalyst then enter reaction zone IV together.

In reaction zone IV, the $C_5$ hydrocarbons feedstock S4 from the present process comes into contact with the catalyst and stream from reaction zone III and reacts under a reaction temperature between about 490° C. and about 640° C., a WHSV between about 20 $h^{-1}$ and about 750 $h^{-1}$, an catalyst/oil ratio between about 3 and about 20 by weight, and a reaction pressure between about 0.12 MPa and about 0.6 MPa (absolute pressure). The reaction product and catalyst then enter reaction zone V together.

In reaction zone V, a part of feedstock and $C_5$ hydrocarbons feedstock S5 from the present process come into contact and mix with the catalyst and stream from reaction zone IV, spent catalyst C5 from pipeline P5, regenerated catalyst C4 from pipeline P4, and the catalyst and reaction product after regenerated catalyst C3 from pipeline P3 contacts and reacts with propane PS3, and react under a reaction temperature between about 510° C. and about 700°

C., a WHSV between about 1 h$^{-1}$ and about 100 h$^{-1}$, an catalyst/oil ratio between about 3 and about 50 by weight, and a reaction pressure between about 0.12 MPa and about 0.6 MPa (absolute pressure). The reaction product and catalyst then enter reaction zone VI together.

In reaction zone VI, C$_6$ feedstock S6 from the present process comes into contact and mixes with the catalyst and stream from reaction zone V and reacts under a reaction temperature between about 510° C. and about 700° C., a WHSV between about 20 h$^{-1}$ and about 700 h$^{-1}$, an catalyst/oil ratio between about 3 and about 50 by weight, and a reaction pressure between about 0.12 MPa and about 0.6 MPa (absolute pressure). The reaction product and catalyst then enter reaction zone VII together.

In reaction zone VII, water or steam S7 comes into contact and mixes with the catalyst and stream from reaction zone VI and reacts under a reaction temperature between about 450° C. and about 700° C., a WHSV between about 20 h$^{-1}$ and about 700 h$^{-1}$, an catalyst/oil ratio between about 3 and about 50 by weight, and a reaction pressure between about 0.12 MPa and about 0.6 MPa (absolute pressure). The reaction products vapor and catalyst then enter the catalyst/products vapor separation system. The separated product vapor enters the product vapor separation system and the catalyst enters the regenerator for generation optionally after being stripped.

Figure 2:
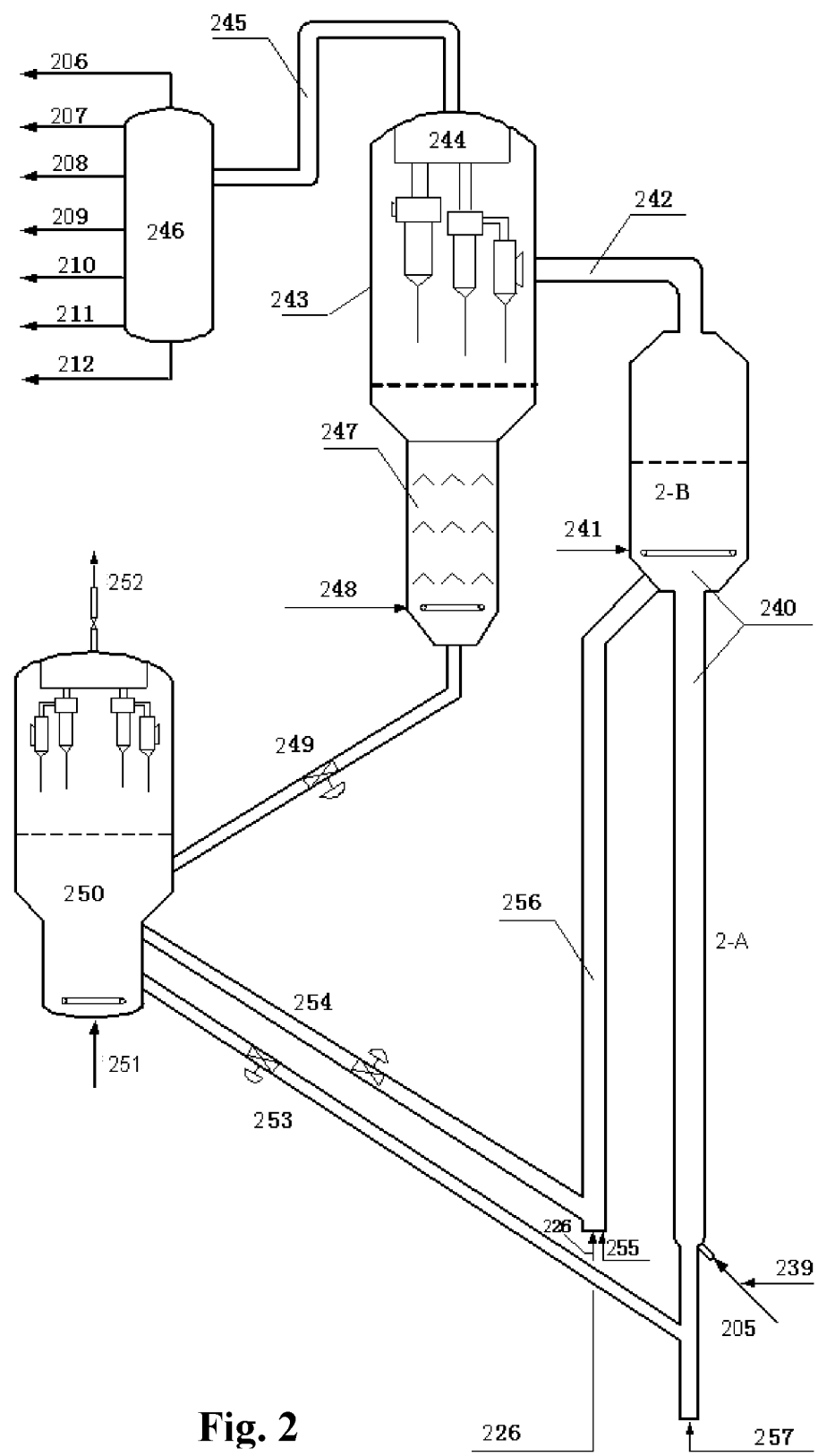
FIG. 2 is a schematic diagram of another example catalytic cracking process of technical scheme 1.

FIG. 2 illustrates a schematic diagram of example catalytic cracking process of technical scheme 1.

In this process, the catalytic cracking reactor 240 includes the first reaction zone, i.e. riser 2-A, the second reaction zone, i.e. fluidized bed 2-B in series. The difference between the reaction temperature of the second reaction zone and that of the first reaction zone is about 10° C.-200° C., preferably about 20° C.-100° C., and the ratio of the WHSV of the second reaction zone to that of the first reaction zone is about 1:1.1-1:750, preferably about 1:1.1-1:300.

In the example, the process flow is as follows:

The pre-lifting steam enters from the bottom of riser 2-A through pipeline 257 and the regenerated catalyst move upward along riser 2-A with increasing velocity under the pre-lifting action of the steam. The feedstock is injected into riser 2-A through pipeline 205 together with atomizing steam from pipeline 239 and comes into contact with the regenerated catalyst. After being lifted by the steam from pipeline 255, the regenerated catalyst from pipeline 254 enters the vertical transfer line 256 together with C$_2^0$-C$_3^0$ and C$_4$-C$_8$ from pipeline 226 and moves upward, and finally enters fluidized bed 2-B to carry out reaction together with the product vapor and catalyst from riser 2-A.

Steam enters the bottom of fluidized bed 2-B through pipeline 241 to ensure the fluidization and reaction of fluidized bed 2-B. The product vapor produced in fluidized bed 2-B and the deactivated spent catalyst enter the cyclone in disengager 243 through pipeline 242 to carry out the separation of the spent catalyst from the product vapor. The product vapor enters collection chamber 244 and the catalyst fine powder returns to the disengager through the leg. The spent catalyst in the disengager flows towards stripping section 247 and comes into contact with the steam from pipeline 248. The product vapor stripped from the spent catalyst enters chamber 244 through the cyclone. The spent catalyst after stripping enters regenerator 250 through sloped pipe 249. The main air through 251 enters the regenerator to burn off coke on the spent catalyst and regenerate the deactivated spent catalyst, and the stack gas enters the fume machine through pipeline 252.

The regenerated catalyst is divided into two parts, wherein one part enters riser 2-A through sloped pipe 253 and the other part enters fluidized bed 2-B sequentially through sloped pipe 254 and vertical transfer line 256 for recycle use. The product vapor in chamber 244 enter subsequent separation system 246, wherefrom the ethylene and propylene obtained through separation are withdrawn through pipeline 207, the catalytic cracking dry gas (i.e. hydrogen and methane) is withdrawn through pipeline 206, the catalytic cracking C$_2^0$-C$_3^0$ is withdrawn through pipeline 208 and finally introduced into vertical transfer line 226, the catalytic cracking C$_4$-C$_5$ is withdrawn through pipeline 209, the catalytic cracking naphtha is withdrawn through pipeline 210 to separate aromatics such as toluene, xylene, etc, the catalytic cracking diesel is withdrawn through pipeline 211, the catalytic cracking cycle oil and slurry are withdrawn through pipeline 212. The catalytic cracking C$_4$-C$_5$ returns to fluidized bed 2-B sequentially through pipeline 226 and vertical transfer line 256. The diesel or hydrotreated diesel, catalytic cracking cycle oil, and slurry returns to riser 2-A together through pipeline 205.

Figure 3:
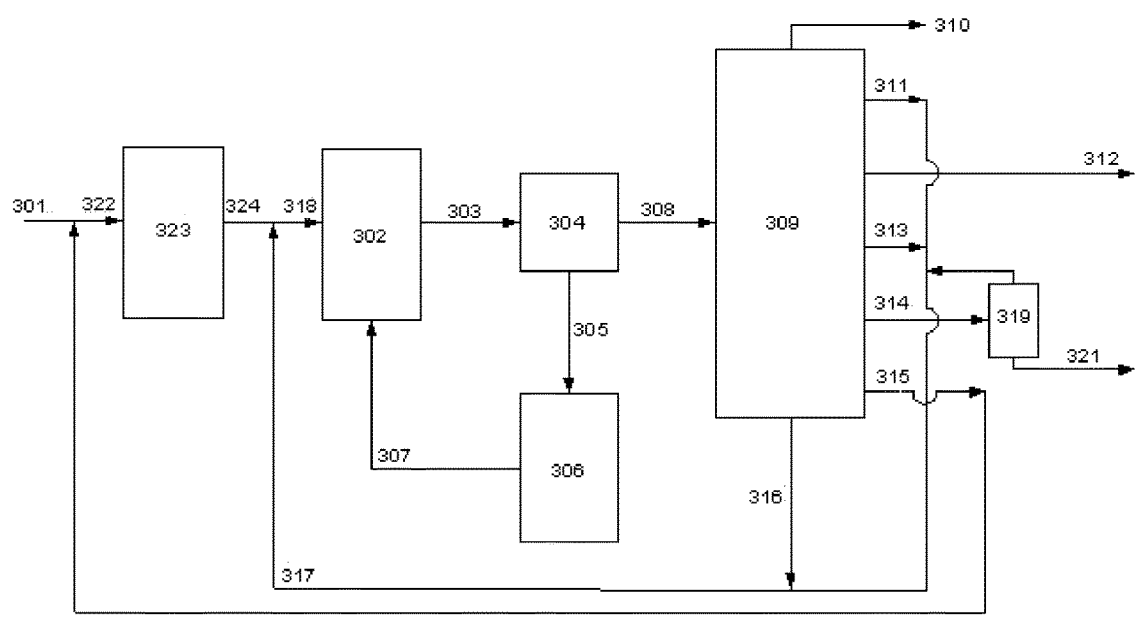
FIG. 3 is a schematic example flowsheet of the process of technical scheme 2.

FIG. 3 illustrates a schematic example flowsheet of the process of technical scheme 2.

In this example, the feedstock mixes through pipeline 301 with the cycle oil from pipeline 315 enters hydrotreating unit 323 through pipeline 322, comes into contact with the hydrotreating catalyst and hydrogen, and reacts under the conditions of a hydrogen partial pressure between about 3.0 MPa and 20.0 MPa, a reaction temperature between about 300° C. and about 450° C., a hydrogen/oil ratio between about 300 and about 2000 by volume, and a LHSV between about 0.1 h$^{-1}$ and about 3.0 h$^{-1}$. The oil produced in the hydrotreating unit mixes through pipeline 324 with the recycle stream from pipeline 317, then enters catalytic cracking reactor 302 through pipeline 318, comes into contact with catalytic cracking catalyst and steam, and reacts under the conditions of a temperature between about 500° C. and about 700° C., a pressure between about 0.15-0.4 MPa (absolute pressure), a ratio of the catalytic cracking catalyst to catalytic cracking feedstock between about 5 and about 50 by weight, a ratio of steam to catalytic cracking feedstock between about 0.05 and about 1.0 by weight. The coked spent catalyst and reaction product vapor enters catalyst/oil separator 304 through pipeline 303, the separated spent catalyst enters regenerator 306 through pipeline 305.

The catalyst regenerated by burning off coke possesses higher activity and selectivity, which returns to reactor 302 through pipeline 307, and the reaction product vapor enters product separator 309 through pipeline 308. The separated ethylene and propylene are withdrawn through pipeline 312, and the cracked naphtha from which C5-C6 is removed enters solvent extraction unit 319. The extraction raffinate from the solvent extraction unit 319 is withdrawn via pipeline 320. The obtained aromatics are withdrawn through pipeline 321, hydrogen and methane are withdrawn through pipeline 310, ethane and propane are withdrawn through pipeline 311, C4-C6 are withdrawn through pipeline 313, the cycle oil is withdrawn through pipeline 315, and the slurry is withdrawn through pipeline 316. Ethane and propane, C4-C6, the extraction raffinate of naphtha, and slurry are all or partly return to catalytic cracking reactor 302 sequentially through pipelines 317 and 318, and the cycle oil return to hydrotreating unit 323 sequentially through pipelines 315 and 322.

Figure 4:
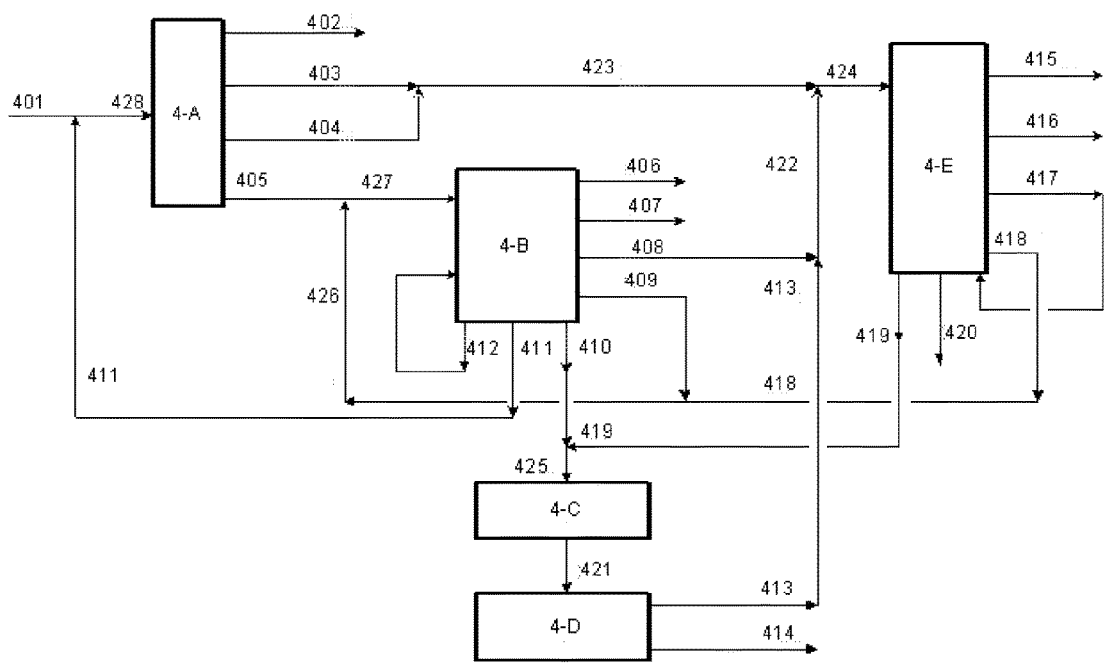
FIG. 4 is a schematic example flowsheet of the process and apparatus of technical scheme 3.

FIG. 4 illustrates a schematic example flowsheet of the process and apparatus of technical scheme 3.

In this example, feedstock mixes through pipeline 401 with diesel from pipeline 411 then enters hydrogenation unit 4-A through pipeline 428. $H_2$, $CH_4$, hydrotreated $C_2^0$-$C_4^0$, hydrotreated naphtha, and hydrotreated product obtained by hydrotreating are withdrawn from pipelines 402, 403, 404, and 405, respectively. The hydrotreated $C_2^0$-$C_4^0$ and hydrotreated naphtha mixes respectively through pipelines 403 and 404 then enters steam cracking unit 4-E sequentially through pipelines 423 and 424. The hydrotreated product as a feedstock for catalytic cracking mixes with $C_4$-$C_5$ from pipeline 426, enters catalytic cracking unit 4-B and reacts under the conditions of a temperature between about 500° C. and about 700° C., a pressure between about 0.15-0.4 MPa (absolute pressure), a ratio of the catalytic cracking catalyst to catalytic cracking feedstock between about 5 and about 50 by weight, a ratio of steam to catalytic cracking feedstock between about 0.05 and about 1.0 by weight. $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, diesel, cycle oil obtained in catalytic cracking unit 4-B are withdrawn from pipelines 406, 407, 408, 409, 410, 411, and 412, respectively. $C_2^=$-$C_3^=$ is one of the desired product.

The $C_2^0$-$C_3^0$ as one of the steam cracking feedstocks enters steam cracking unit 4-E sequentially through pipelines 408, 422, and 424. The catalytic cracking $C_4$-$C_5$ mixes through pipeline 409 with steam cracking $C_4$-$C_5$ from pipeline 418 then returns to catalytic cracking unit 4-B sequentially through pipelines 426 and 427. The catalytic cracking naphtha mixes with steam cracking naphtha from pipeline 419 then enters selective hydrogenation unit 4-C through pipeline 425. The diesel returns to hydrogenation unit 4-A sequentially through pipelines 411 and 428. The cycle oil returns to catalytic cracking unit 4-B through pipeline 412. The stream from selective hydrogenation unit 4-C enters solvent extraction unit 4-D through pipeline 421. The BTX obtained in solvent extraction unit 4-D are withdrawn from pipeline 414 as desired products, and the extraction raffinate enters steam cracking unit 4-E sequentially through pipelines 413, 422, and 424.

The hydrotreated $C_2^0$-$C_4^0$, hydrotreated naphtha, catalytic cracking $C_2^0$-$C_3^0$, and extraction raffinate first mix respectively through pipelines 403, 404, 408, and 413, and then enter steam cracking unit 4-E through pipeline 424. $H_2$, $CH_4$, steam cracked $C_2^=$-$C_3^=$, steam cracked $C_2^0$-$C_3^0$, steam cracked $C_4$-$C_5$, steam cracked naphtha, and fuel oil are withdrawn respectively through pipelines 415, 416, 417, 418, 419, and 420, wherein the steam cracked $C_2^=$-$C_3^=$ is withdrawn from the unit through pipeline 416 as one of the desired products, the steam cracked $C_2^0$-$C_3^0$ returns to steam cracking unit 4-E through pipeline 417, the steam cracked $C_4$-$C_5$ enters catalytic cracking unit 4-B sequentially through pipelines 418, 426, and 427, and the steam cracked naphtha enters selective hydrogenation unit 4-C through pipeline 419.

The disclosed examples provide the benefit of increasing the yield of light olefins, such as propylene, ethylene, etc., wherein the yield of propylene exceeds 20% by weight, preferably exceeds 25%, and more preferably exceeds 30%. The example processes can also produce joint products, aromatics rich in toluene, xylene, etc. Therefore, a technical breakthrough of the refinery concept is realized, i.e., a conversion of the refinery from conventional fuel and fuel-lubricant production mode into chemical industry mode and a development and extension of the refinery from single oil refining to the production of downstream products with high added values. This conversion not only solves the problem of the shortage of the chemical feedstocks, but also increases the benefit of the refinery.

The following examples will further describe the present invention but not limit it.

The feedstock used in the examples is VGO, the properties are shown in Table 1, and the solvent used in the examples is sulfolane.

The process for preparing the catalytic cracking catalyst used in the examples is briefly described as follows:

1) 20 g of $NH_4Cl$ was dissolved in 1000 g of water, whereto 100 g (dry basis) of crystallized product ZRP-1 zeolite (produced in the Catalyst Plant of Qilu Petrochemicals Co., $SiO_2/Al_2O_3$=30, content of rare earths $RE_2O_3$=4.0% by weight) was added, and a filter cake was obtained after exchanging at 90° C. for 0.5 hour and filtration. The filter cake was impregnated with a solution of 4.0 g of $H_3PO_4$ (with a concentration of 85%) and 4.5 g of $Fe(NO_3)_3$ in 90 g of water and then dried. The resultant solid was calcined at 550° C. for 2 hours to obtain a intermediate pore size zeolite containing phosphor and iron and having the structure of MFI, the composition of which determined by element analysis was $0.1Na_2O.5.1Al_2O_3.2.4P_2O_5.1.5Fe_2O_3.3.8RE_2O_3.88.1SiO_2$.

2) 75.4 kg of halloysite (Product of Suzhou Porcelain Clay Co., solid content 71.6% by weight) was slurried with 250 kg of cation-removed water and 54.8 kg of pseudo-boehmite (industrial product of Shandong Alumina Plant, solid content 63% by weight) was added. PH is adjusted at 2-4 with hydrochloric acid, the slurry was uniformly stirred, and laid aside for aging at 60-70° C. for 1 hour. The temperature was lowered down to below 60° C. while maintaining the pH at 2-4, and then 4.5 kg of alumina sol (industrial product of Shandong Alumina Plant, $Al_2O_3$ content 21.7% by weight) was added. A mixed slurry was obtained after stirring for 40 min.

3) The intermediate pore size zeolite containing phosphor and iron and having the structure of MFI prepared in step 1) (dry basis 45 kg) and DASY zeolite (industrial product of the Catalyst Plant of Qilu Petrochemicals Co., unit cell size 2.445-2.448 nm, $RE_2O_3$ content 2.0%, dry basis 7.5 kg) were added to the mixed slurry obtained in step 2) and uniformly stirred. The resulted slurry was shaped by spray drying, and the product was washed with a solution of ammonium dihydrogen phosphate (phosphor content 1% by weight) to remove free Na+. After drying, a sample of the catalytic cracking catalyst was obtained. The composition of the catalyst was 30% by weight of MFI structure intermediate pore size zeolite containing phosphor and iron, 5% by weight of DASY zeolite, 23% by weight of pseudo-boehmite, 6% by weight of alumina sol, and balanced kaolin.

The process for preparing the hydrotreating catalyst used in the examples is briefly described as follows. Ammonium metatungstate (($NH_4W_4O_{13}.18H_2O$, chemically pure) and nickel nitrate ($Ni(NO_3)_2.6H_2O$, chemically pure) were dissolved in water to prepare 200 ml of solution. 50 g of alumina support was added to the solution and impregnated at room temperature for 3 hours. During impregnation, the impregnating solution was treated with an ultrasonic instrument for 30 min, and then cooled, filtered and dried in a microwave oven for about 15 min. The composition of the catalyst was 30% by weight of $WO_3$, 3.1% by weight of NiO, and balanced Alumina.

The process for preparing the hydrotreating catalyst used in the examples is briefly described as follows. Ammonium metatungstate (($NH_4W_4O_{13}.18H_2O$, chemically pure) and nickel nitrate ($Ni(NO_3)_2.6H_2O$, chemically pure) were dissolved in water to prepare 200 mL of solution. 100 g of alumina support was added to the solution and impregnated at room temperature for 4 hours. After separation, the wet catalyst was dried in a oven for 4 hours and calcined in a tube furnace with blowing air at 500° C. for 4 hours. The composition of the catalyst was 25.3% by weight of $WO_3$, 2.3% by weight of NiO, and balanced alumina.

Example 1

The experiment of the present example was carried out according to the flow in FIG. 1. Feedstock A was directly used as the feedstock of catalytic cracking and the experiment was carried out in seven reaction zones consisting of risers and fluidized beds. The reaction temperatures of reaction zones I, II, III, IV, V, VI, and VII sequentially were 530° C., 520° C., 550° C., 540° C., 640° C., 620° C., and 580° C., and the WHSVs of reaction zones I, II, III, IV, V, VI, and VII sequentially were 360 $h^{-1}$, 720 $h^{-1}$, 20 $h^{-1}$, 180 $h^{-1}$, 5 $h^{-1}$, 200 $h^{-1}$, and 620 $h^{-1}$, wherein the reaction temperatures of reaction zones III and V were 20° C. and 110° C. higher than that of reaction zone I respectively, the ratio of WHSVs of reaction zones III and V (fluidized bed) to that of reaction zone I (riser) were 1:18 and 1:72 respectively, and the heats supplemented to reaction zones III and V account for 11% and 60% of the reaction heat of the total reaction system respectively. Finally, the products were separated, wherein $C_3$-$C_5$ was cycled to the fluidized beds. The operating conditions of reaction zones I, III, and V, and product distribution are shown in Table 2.

It can be seen from Table 2 that the yields of propylene and ethylene attain as high as 35.21% and 14.56% by weight respectively, and those of toluene and xylene are 3.95% and 4.26% by weight respectively.

Example 2

The experiment of the present example was carried out according to the flow in FIG. 2. Feedstock B was directly used as the feedstock of catalytic cracking and the experiment was carried out in a medium-sized riser plus a fluidized bed reactor, wherein the reaction temperature of the fluidized bed was 30° C. higher than that of the riser, the ratio of the WHSV of the fluidized bed to that of the riser was 1:360, and the heat supplemented to the fluidized bed account for 22% of the reaction heat of the total reaction system. Finally, the products were separated, wherein only the slurry was cycled to the riser and $C_4$-$C_6$ was cycled to the fluidized bed, but the other stream were not cycled. The operating conditions of catalytic cracking and product distribution are shown in Table 2.

It can be seen from Table 2 that the yields of propylene and ethylene are as high as 30.46% and 18.31% by weight respectively, and those of toluene and xylene are 2.45% and 7.38% by weight respectively.

Example 3

The experiment of the present example was carried out according to the flow in FIG. 3. Feedstock A was first subjected to hydrotreating, and the hydrotreated product (the content of hydrogen increased from 12.40% to 13.54% by weight and the content of aromatics decreased from 44.1% to 20.0% by weight) was used as the feedstock of catalytic cracking. The experiment was carried out in a medium-sized riser plus a fluidized bed reactor, wherein the reaction temperature of the fluidized bed was 40° C. higher than that of the riser, the ratio of the WHSV of the fluidized bed to that of the riser was 1:30, and the heat supplemented to the fluidized bed account for 25% of the reaction heat of the total reaction system. Finally, the products were separated, wherein only the slurry was cycled to the riser, but the other stream was not cycled. The operating conditions of hydrotreating and catalytic cracking and product distribution are shown in Table 3.

It can be seen from Table 3 that the yields of propylene and ethylene are as high as 32.97% and 12.63% by weight respectively, and those of toluene and xylene are 1.93% and 4.05% by weight respectively.

Example 4

The experiment of the present example was carried out according to the flow in FIG. 4. The reactor for catalytic cracking is a riser plus a fluidized bed reactor in a pilot plant, wherein the reaction temperature of the fluidized bed was 40° C. higher than that of the riser, the ratio of the WHSV of the fluidized bed to that of the riser was 1:30, and the heat supplemented to the fluidized bed account for 30% of the reaction heat of the total reaction system. Finally, the products were separated, wherein only the slurry was cycled to the riser, but the other stream was not cycled. All the hydrotreating, catalytic cracking, selective hydrogenation and solvent extraction experiments were carried out in corresponding middle-sized units.

The feedstock used in the present example was the same as that in Example 3, i.e. feedstock A, and the operating conditions and product distribution are shown in Table 3. It can be seen from Table 3 that the yields of propylene and ethylene are as high as 40.65% and 20.64% by weight respectively, and those of toluene and C8 aromatics are 4.34% and 5.18% by weight respectively.

TABLE 1

|  | Examples 1, 3, 4 | Example 2 |
|---|---|---|
| No. of feedstock | A | B |
| Property of feedstock |  |  |
| Density (20° C.), g/cm$^3$ | 0.8886 | 0.9134 |
| Sulfur content, ppm | 4700 | 5800 |
| Nitrogen content, ppm | 1600 | 2900 |
| Aromatics, m % | 26.3 | 32.6 |
| C, m % | 86.46 | 86.23 |
| H, m % | 12.86 | 12.69 |
| Boiling range |  |  |
| (ASTM D-1160), ° C. |  |  |
| IBP | 312 | 327 |
| 10% | 361 | 363 |
| 30% | 412 | 409 |
| 50% | 452 | 450 |
| 70% | 478 | 482 |
| 90% | 506 | 504 |
| 95% | 532 | 526 |
| FBP | 546 | 542 |

TABLE 2

|  | Example1 | Example 2 | Example 3 |
|---|---|---|---|
| No. of feedstock | A | B | A |
| Hydrotreating unit |  |  |  |
| Operation condition |  |  |  |
| Reaction temperature, ° C. | — | — | 370 |
| Hydrogen partial pressure, MPa | — | — | 14.0 |
| LHSV, $h^{-1}$ | — | — | 0.6 |
| Hydrogen/oil ratio, v/v | — | — | 800 |

TABLE 2-continued

|  | Example 1 | Example 2 | Example 3 |
|---|---|---|---|
| Product distribution, m % | | | |
| Gas | — | — | 2.55 |
| Naphtha | — | — | 1.80 |
| Hydrotreated product | — | — | 96.90 |
| Catalytic cracking unit Operation condition | | | |
| Riser | reaction zone I | | |
| Reaction temperature, °C. | 530 | 650 | 580 |
| Catalyst/oil ratio, m/m | 8 | 20 | 12 |
| WHSV, h$^{-1}$ | 360 | 180 | 120 |
| Steam injected (to feed), m % | 20 | 10 | 15 |
| Fluidized bed | reaction zone III/V | | |
| Reaction Temperature, °C. | 550/640 | 680 | 620 |
| Catalyst/oil ratio, m/m | 10/30 | 45 | 25 |
| WHSV, h$^{-1}$ | 20/5 | 0.5 | 4 |
| Water injected (to feed), m % | 20/25 | 60 | 30 |
| Temperature difference between riser and the bed, °C. | 20/110 | 30 | 40 |
| WHSV ratio (the fluidized bed/riser) | 1:18/1:72 | 1:360 | 1:30 |
| Product distribution, m % | | | |
| H$_2$ & CH$_4$ | 5.46 | 6.47 | 4.36 |
| Ethylene | 14.56 | 18.31 | 12.63 |
| Propylene | 35.21 | 30.46 | 32.97 |
| Ethane & propane | 4.23 | 5.17 | 4.73 |
| C$_4$ | 4.54 | 0 | 18.68 |
| C$_5$-C$_6$ | 2.53 | 0 | 1.86 |
| Toluene | 3.95 | 2.45 | 1.93 |
| Xylene | 4.26 | 7.38 | 4.05 |
| Other single-ring aromatics | 2.78 | 9.76 | 3.86 |
| Extraction raffinate of pyrolyzed naphtha | 5.59 | 1.84 | 1.09 |
| Cycle oil | 7.04 | 8.68 | 3.50 |
| Slurry | 0 | 0 | 2.28 |
| Coke | 9.85 | 9.48 | 8.06 |

TABLE 3

|  | Example 4 |
|---|---|
| Hydrotreating unit | |
| Reaction temperature, °C. | 370 |
| Hydrogen partial pressure, MPa | 14.0 |
| LHSV, h$^{-1}$ | 0.6 |
| H$_2$/oil ratio, v/v | 800 |
| Catalytic cracking unit Riser | |
| Reaction temperature, °C. | 580 |
| Catalyst/oil ratio, m/m | 12 |
| WHSV, h$^{-1}$ | 120 |
| Water injected (ratio to feed), m % | 15 |
| Fluidized bed | |
| Reaction temperature, °C. | 620 |
| Catalyst/oil ratio, m/m | 25 |
| WHSV, h$^{-1}$ | 4 |
| Water injected (ratio to feed), m % | 30 |
| Temperature difference between the fluidized bed/riser, °C. | 40 |
| WHSV ratio (the fluidized bed/riser) | 1:30 |
| Selective hydrogenation unit | |
| Reaction temperature, °C. | 200 |
| Hydrogen partial pressure, MPa | 4.0 |
| LHSV, h$^{-1}$ | 2.5 |
| Hydrogen/oil ratio, v/v | 350 |
| Solvent extraction unit | |
| Temperature, °C. | 90 |
| Solvent ratio, v/v | 3.5 |
| Yield of product, m % | |
| Methane & hydrogen | 8.60 |
| Ethylene | 20.64 |
| Propylene | 40.65 |
| Benzene | 1.28 |
| Toluene | 4.34 |
| C$_8$ aromatics | 5.18 |
| C$_9^+$ heavy aromatics | 6.03 |
| Fuel oil | 2.5 |
| Coke | 10.78 |

What is claimed is:

1. A process for producing light olefins and aromatics, comprising the steps of:
   (1) reacting a feedstock with a hydrotreating catalyst and hydrogen in a hydrotreating unit under the conditions of a hydrogen partial pressure between about 3.0 MPa and 20.0 MPa, a reaction temperature between about 300° C. and 450° C., a hydrogen/oil ratio between about 300 and 2000 by volume, and a liquid hourly space velocity (LHSV) between about 0.1 h$^{-1}$-3.0 h$^{-1}$, and separating a reaction effluent to obtain a hydrotreated product and hydrogen, wherein the hydrogen enters a recycle stream that is fed into the hydrotreating unit; and
   (2) catalytically cracking in a catalytic cracker the hydrotreated product under conditions of a reaction temperature between about 400° C. and 800° C. and a weight hourly space velocity (WHSV) between about 0.1 h$^{-1}$ and 750 h$^{-1}$,
   wherein the catalytic cracker comprises a first reaction zone, a final reaction zone, and optionally one or more reaction zones disposed between the first reaction zone and the final reaction zone,
   wherein the catalytic cracking of the hydrotreated product in Step (2) comprises:
   introducing the hydrotreated product and a catalytic cracking catalyst into the first reaction zone;
   introducing substantially all effluent from the first reaction zone into a reaction zone downstream from the first reaction zone;
   obtaining a spent catalyst and a reaction product stream from the final reaction zone;
   separating the spent catalyst from the reaction product stream;
   regenerating the spent catalyst to produce a regenerated catalyst;
   introducing the regenerated catalyst into the catalytic cracker,
   wherein a reaction temperature in a reaction zone downstream from the first reaction zone is higher than that of the first reaction zone,
   wherein values of WHSV in the catalytic cracker range from 0.1 h$^{-1}$ and 750 h$^{-1}$ and the WHSV of a reaction zone downstream from the first reaction zone is lower than that of the first reaction zone.

2. The process according to claim 1, wherein the hydrotreating catalyst in the step (1) is a catalyst comprising one or more non-noble metal selected from a group consisting of Group VIB and Group VIII elements supported on a support selected from the group consisting of alumina, an amorphous silica-alumina, and combinations thereof.

3. The process according to claim 2, wherein said non-noble metal of Group VIB is Mo, W, or both and that of Group VIII is Co, Ni, or both.

4. A process for producing light olefins and aromatics, comprising the steps of:
(1) hydrotreating a feedstock in the presence of hydrotreating hydrogen and a hydrotreating catalyst under the conditions of a hydrogen partial pressure between about 3.0 MPa and 20.0 MPa, a reaction temperature between about 300° C. and 450° C., a hydrogen/oil volume ratio between about 300-2000, and a liquid hourly space velocity (LHSV) between about $0.1\ h^{-1}$-$3.0\ h^{-1}$, and separating a reaction effluent to obtain $H_2$, $CH_4$, hydrotreated $C_2^0$-$C_4^0$, hydrotreated naphtha, and a hydrotreated product, wherein the $H_2$ reaction effluent is reused for reaction with the feedstock;
(2) catalytically cracking the hydrotreated product in a catalytic cracking reactor under conditions of a reaction temperature between about 400° C. and 800° C. and a weight hourly space velocity (WHSV) between about $0.1\ h^{-1}$ and $750\ h^{-1}$, separating spent catalyst from a reaction product vapor, and stripping and regenerating the spent catalyst for reuse, separating a reaction product vapor to obtain $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, LCO, and heavy cycle oil (HCO), and cycling the $C_4$-$C_5$, LCO, and HCO into the catalytic cracking reactor;
(3) steam cracking the hydrotreated $C_2^0$-$C_4^0$ and hydrotreated naphtha of step (1) and catalytic cracking $C_2^0$-$C_3^0$ of step (2) in a steam cracking unit under a temperature between about 700° C.-1000° C. to produce a stream cracking product and separating the stream cracking product to obtain $H_2$, $CH_4$, steam cracking $C_2^=$-$C_3^=$, steam cracking $C_2^0$-$C_3^0$, steam cracking $C_4$-$C_5$, steam cracking naphtha, and fuel oil, wherein the steam cracking $C_4$-$C_5$ are cycled to the catalytic cracking reactor;
(4) selectively hydrogenating the catalytic cracking naphtha of step (2) and the steam cracking naphtha of step (3) to produce a hydrogenated naphtha, and separating the hydrogenated naphtha in a solvent extraction unit to obtain an aromatics stream and an extraction raffinate, and feeding the extraction raffinate to the steam cracking unit for steam cracking,
wherein the catalytic cracker comprises a first reaction zone, a final reaction zone, and optionally one or more reaction zones disposed between the first reaction zone and the final reaction zone,
wherein the catalytic cracking of the hydrotreated product in Step (2) comprises:
introducing the hydrotreated product and a catalytic cracking catalyst into the first reaction zone;
introducing substantially all effluent from the first reaction zone into a reaction zone downstream from the first reaction zone,
wherein a reaction temperature in a reaction zone downstream from the first reaction zone is higher than that of the first reaction zone, and
wherein a WHSV of a reaction zone downstream from the first reaction zone is lower than that of the first reaction zone.

5. The process according to claim 4, wherein the conditions for steam cracking in step (3) include a residence time for reaction between about 0.05 seconds and 0.6 seconds, and a steam to oil ratio between about 0.1-1.0 by weight.

6. The process according to claim 4, wherein the conditions for selective hydrogenation of step (4) include a hydrogen partial pressure between about 1.2 MPa and 8.0 MPa, a reaction temperature between about 150° C. and 300° C., a hydrogen to oil ratio between about 150 and 600 by volume, and a LHSV between about $1\ h^{-1}$ and $20\ h^{-1}$.

7. The process according to claim 4, wherein a solvent in the solvent extraction unit of step (4) is one selected from the group consisting of sulfolane, N-methyl pyrrolidone, diethyl glycol ether, triethyl glycol ether, tetraethyl alcohol, dimethyl sulfoxide, and N-formyl morpholine, and mixtures thereof.

8. The process according to claim 4, wherein the temperature for the solvent extraction in step (4) is about 80° C.-120° C. and a solvent to feed ratio is about 2-6 by volume.

* * * * *